(12) United States Patent
Connolly

(10) Patent No.: US 11,067,529 B2
(45) Date of Patent: Jul. 20, 2021

(54) MULTI-ZONE, FIXED POTENTIAL TEST SENSOR HEATING SYSTEM

(71) Applicant: Jim Connolly, Indianapolis, IN (US)

(72) Inventor: Jim Connolly, Indianapolis, IN (US)

( * ) Notice: Subject to any disclaimer, the term of this patent is extended or adjusted under 35 U.S.C. 154(b) by 162 days.

(21) Appl. No.: 16/196,547

(22) Filed: Nov. 20, 2018

(65) Prior Publication Data

US 2019/0154619 A1 May 23, 2019

Related U.S. Application Data

(60) Provisional application No. 62/589,653, filed on Nov. 22, 2017.

(51) Int. Cl.
| | | |
|---|---|---|
| *G01N 27/327* | (2006.01) | |
| *C12Q 1/00* | (2006.01) | |
| *B01L 7/00* | (2006.01) | |

(52) U.S. Cl.
CPC ............ *G01N 27/3272* (2013.01); *B01L 7/54* (2013.01); *C12Q 1/001* (2013.01); *G01N 27/327* (2013.01); *G01N 27/3273* (2013.01); *B01L 2300/0645* (2013.01); *B01L 2300/0887* (2013.01); *B01L 2300/1827* (2013.01)

(58) Field of Classification Search
CPC ....... G01N 27/327–3278; G01N 27/406–4118
USPC .................. 204/403.01–403.15, 421–429; 205/777.5–778, 792; 73/23.31–23.33
See application file for complete search history.

(56) References Cited

U.S. PATENT DOCUMENTS

| | | | | |
|---|---|---|---|---|
| 6,392,209 B1 * | 5/2002 | Oppitz | ................... | H05B 3/146 219/549 |
| 6,475,360 B1 * | 11/2002 | Hodges | .............. | G01N 27/3272 204/403.01 |
| 7,306,283 B2 * | 12/2007 | Howick | ............... | B60N 2/5678 297/180.12 |
| 2005/0195488 A1 * | 9/2005 | McCabe | ................. | G02F 1/161 359/603 |

(Continued)

FOREIGN PATENT DOCUMENTS

| | | | |
|---|---|---|---|
| EP | 0313390 | | 4/1989 |
| JP | 03166701 | * | 7/1991 |

(Continued)

OTHER PUBLICATIONS

Patent Cooperation Treaty, Int'l Search Report & Written Opinion, Form PCT/ISA/220 (dated Jul. 2017).

*Primary Examiner* — Bach T Dinh
(74) *Attorney, Agent, or Firm* — Blanchard & Associates

(57) ABSTRACT

A test sensor heating system is disclosed that provides the desired and different temperatures to at least two different reaction zones based on a fixed potential. The measurement device does not alter the potential applied to the heating system in response to temperature feedback information. The heating system provides the desired and different temperatures to the different reaction zones of the test sensor by varying heating element spacing and/or the resistivity of an associated resistive layer of the test sensor to provide the desired temperature in response to the fixed potential. The system also may provide two or more different temperature zones to the test sensor by using different heating element spacing and/or resistive layer resistivity at different locations of the test sensor.

26 Claims, 7 Drawing Sheets

(56) References Cited

U.S. PATENT DOCUMENTS

| | | | |
|---|---|---|---|
| 2007/0000780 A1* | 1/2007 | Oya | G01N 27/419 |
| | | | 204/424 |
| 2009/0000947 A1 | 1/2009 | Akahori et al. | |
| 2009/0090623 A1* | 4/2009 | Chuang | H01B 1/24 |
| | | | 204/403.01 |
| 2011/0102127 A1* | 5/2011 | Schultes | H01C 17/12 |
| | | | 338/223 |
| 2011/0172750 A1* | 7/2011 | Cassidy | A61F 7/007 |
| | | | 607/108 |
| 2013/0010826 A1 | 1/2013 | Le Neel | |
| 2013/0193384 A1* | 8/2013 | Dorfman | C09D 127/16 |
| | | | 252/511 |
| 2014/0051159 A1 | 2/2014 | Bergstedt | |
| 2015/0226689 A1* | 8/2015 | Semancik | B01L 7/52 |
| | | | 205/775 |
| 2016/0131537 A1* | 5/2016 | Aliane | G01K 7/16 |
| | | | 374/185 |
| 2016/0279639 A1 | 9/2016 | Kim | |

FOREIGN PATENT DOCUMENTS

| | | | | |
|---|---|---|---|---|
| KR | 9500009257 | * | 8/1995 | |
| WO | WO-9940411 A1 | * | 8/1999 | A61B 5/14557 |

\* cited by examiner

MULTI-ZONE, FIXED POTENTIAL TEST SENSOR HEATING SYSTEM

REFERENCE TO RELATED APPLICATIONS

This application claims the benefit of U.S. Provisional Application No. 62/589,653 entitled "Multi-Zone, Fixed Potential Test Sensor Heating System" filed Nov. 22, 2017, which is incorporated by reference in its entirety.

BACKGROUND

Biosensor systems provide an analysis of a biological fluid sample, such as whole blood, serum, plasma, urine, saliva, interstitial, or intracellular fluid. The systems generally include a measurement device that analyzes a sample residing in a test sensor. The sample usually is in liquid form. The analysis performed by the biosensor system determines the presence and/or concentration of one or more analytes, such as alcohol, glucose, uric acid, lactate, cholesterol, bilirubin, free fatty acids, triglycerides, proteins, ketones, phenylalanine or enzymes, in the biological fluid. The analysis may be useful in the treatment of physiological abnormalities or insufficiencies. For example, a diabetic individual may use a biosensor system to determine the A1c level in whole blood for adjustments to diet and/or medication.

Biosensor systems may be designed to analyze one or more analytes and may use different volumes of biological fluids. Some systems may analyze a drop of whole blood, such as from 0.25-15 microliters (µL) in volume. Biosensor systems may be implemented using bench-top, portable, and like measurement devices. Portable measurement devices may be hand-held and allow for the identification and/or quantification of one or more analytes in a sample.

Electrochemical biosensor systems usually include a measurement device having electrical contacts that connect with the electrical conductors of a test sensor. The conductors may be made from conductive materials, such as solid metals, metal pastes, conductive carbon, conductive carbon pastes, conductive polymers, and the like. The electrical conductors connect to working and counter electrodes and may connect to reference and/or other electrodes that contact the sample. One or more electrical conductors also may contact the sample to provide functionality not provided by the electrodes. Biosensor systems also may have the ability to determine or estimate temperature, such as with one or more thermocouples or other means.

The measurement device of an electrochemical biosensor system applies an input signal through the electrical contacts to the electrical conductors of the test sensor. The electrical conductors convey the input signal through the electrodes into the sample. The redox reaction of the analyte generates an electrical output signal in response to the input signal. The electrical output signal from the test sensor may be a current (as generated by amperometry or voltammetry), a potential (as generated by potentiometry/galvanometry), or an accumulated charge (as generated by coulometry). The measurement device may have the processing capability to measure and correlate the output signal with the presence and/or concentration of one or more analytes in the sample.

The test sensor of the electrochemical biosensor system has an inlet to introduce the sample and one or more isolated flow paths to direct the sample from the inlet to one or more electrode pairs for analysis. The one or more isolated flow paths are formed between a substrate and a cover. The one or more isolated flow paths may be formed by indentations formed into the substrate, cover, or both, or by a spacer residing between the substrate and the cover including channels through which the sample flows. The substrate, cover, and spacer are generally formed from polymeric materials, with glass or ceramics substituted in some instances. The substrate, cover, and spacer are generally laminated using heat or light energy, but also may be formed as a unit. At least one of the electrode pairs in the one or more isolated flow paths may be energized in the presence of an active enzyme or other species to generate an analyte specific portion of the output signal. Additional reagents that act on the sample may be incorporated into the test sensor between the electrode pair and the inlet of the test sensor.

In electrochemical biosensor systems, the analyte concentration of the sample is determined from an electrical signal generated by an oxidation/reduction or redox reaction of the analyte or a measurable species responsive to the analyte concentration when an input signal is applied to the sample. The input signal may be a potential or current and may be constant, variable, or a combination thereof such as when an AC signal is applied with a DC signal offset. The input signal may be applied as a single pulse or in multiple pulses, sequences, or cycles.

An enzyme or similar species may be added to the sample to enhance the electron transfer from the analyte during the redox reaction. The enzyme or similar species may react with a single analyte, thus providing specificity to a portion of the generated output signal. A redox mediator may be used as the measurable species to maintain the oxidation state of the enzyme and/or assist with electron transfer from the analyte to an electrode. Thus, during the redox reaction, an enzyme or similar species may transfer electrons between the analyte and the redox mediator, while the redox mediator transfers electrons between itself and an electrode of the test sensor.

Electrochemical biosensor systems relying on reaction chemistry that accelerates at higher than room temperature, thus higher than 23 degrees Celsius to 27 degrees Celsius, may be improved with a test sensor having heated reaction zones. A test sensor having a heated reaction zone or zones also permits the use of reaction chemistry on the test sensor that is practically inoperable at room temperature—thus, allowing for analyte determinations to be made with electrochemical test sensors that were not previously possible or practical.

One conventional approach to a heated test sensor is found in U.S. Publication No. 2009/0000947 US to Akahori. Akahori describes a heated test sensor where a temperature sensor in the form of a thermistor is incorporated near the sample analysis area of the test sensor to determine the temperature being generated near the sample analysis area in relation to the voltage applied to the heater member. The thermistor allows the measurement device to vary the voltage of the potential applied to the heater member during the analysis—thus providing active temperature control of the sample analysis area with a variable potential. The system requires a temperature sensor on the test sensor where temperature control is desired and a measurement device capable of varying the potential applied to the heater member in response to temperature information from the temperature sensor.

As seen from the above description, there is an ongoing need for simple and efficient devices and materials for increasing and controlling the temperature of electrochemical biosensor system test sensors. The devices and materials of the present invention overcome at least one of the disadvantages associated with conventional test sensor heating systems, specifically the problem of trying to actively control reaction temperature based on the output from a temperature sensor incorporated near the sample analysis area.

BRIEF DESCRIPTION OF THE FIGURES

The invention can be better understood with reference to the following drawings and description. The components in the figures are not necessarily to scale, emphasis instead being placed upon illustrating the principles of the invention.

Figure 1:
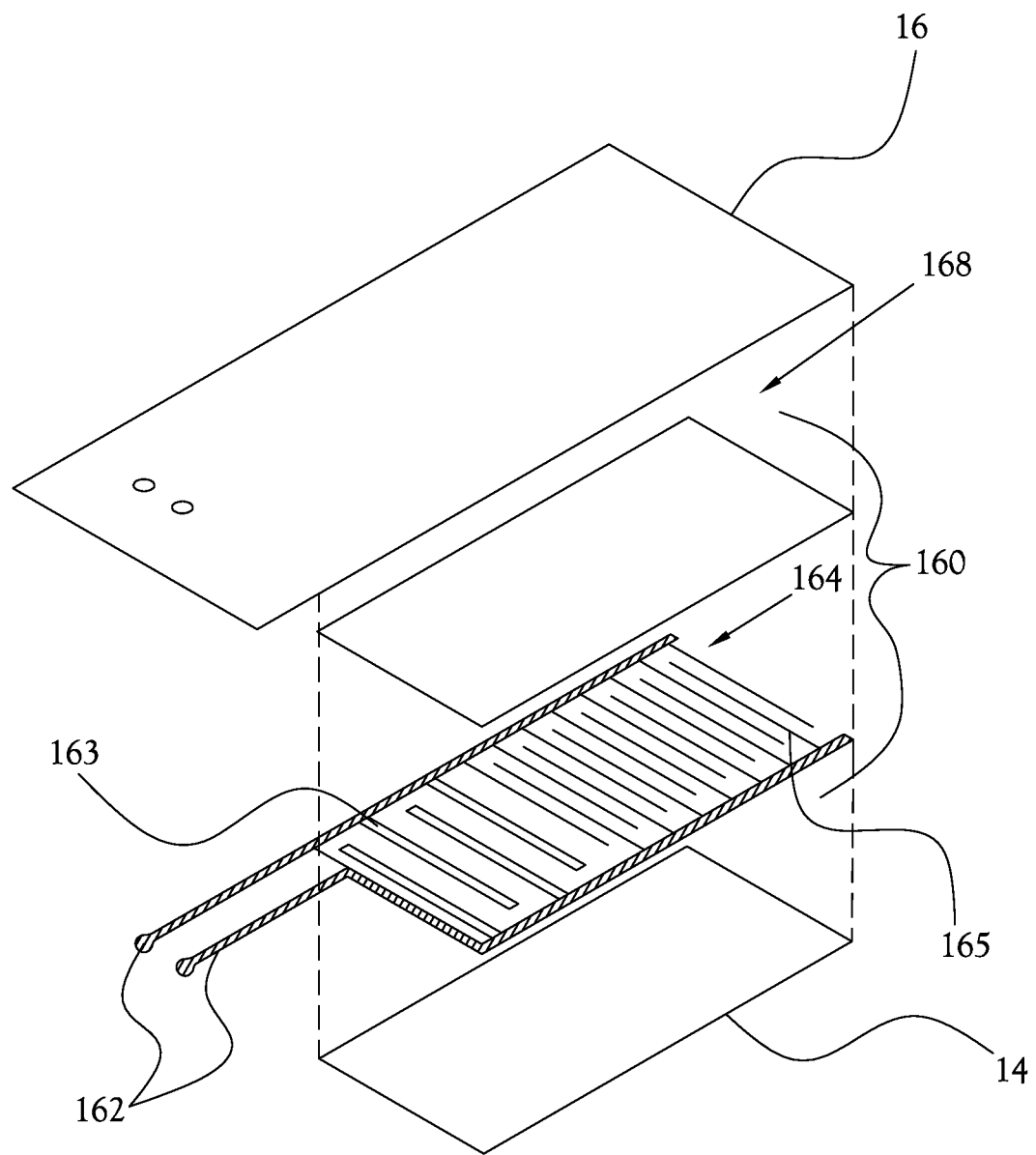
FIG. 1 represents a heating system including electrical heater conductors configured to provide electrical communication between heating elements and the measurement device.

It is noted that the simplified drawings do not illustrate all the various connections and assemblies of the various components; however, those skilled in the art will understand how to implement such connections and assemblies, based on the illustrated components, figures, and descriptions provided herein, using sound engineering judgment.

SUMMARY

In one aspect, the invention provides a reaction zone heating system for a test sensor, the heating system including electrical heater conductors in electrical communication with heating elements, where the electrical heater conductors and the heating elements include a conductive material; at least one resistive layer contacting the heating elements, where the resistive layer includes a mixture of conductive and non-conductive materials; a substrate contacting the at least one resistive layer; and a base contacting the electrical heater conductors and the heating elements.

In another aspect of the invention, there is an electrochemical test sensor for analyzing a sample, the test sensor including an inlet in fluid communication with at least one isolated flow path; a first reaction zone in fluid communication with the inlet; a second reaction zone in fluid communication with the inlet; a reaction zone heating system configured to transmit heat to the first reaction zone and to the second reaction zone, the reaction zone heating system including electrical heater conductors in electrical communication with heating elements, where the electrical heater conductors and the heating elements include a conductive material; at least one resistive layer contacting the heating elements, where the resistive layer includes a mixture of conductive and non-conductive materials; a substrate contacting the at least one resistive layer and forming at least a portion of the inlet and the at least one isolated flow path; and a base contacting the electrical heater conductors and the heating elements.

In another aspect of the invention, there is a method of analyzing a sample with a biosensor system, the method includes inserting a test sensor having at least two reaction zones and a reaction zone heating system into a measurement device, where the reaction zone heating system includes electrical heater conductors in electrical communication with heating elements, where the electrical heater conductors and the heating elements include a conductive material, at least one resistive layer contacting the heating elements, where the resistive layer includes a mixture of conductive and non-conductive materials, a substrate contacting the at least one resistive layer and forming at least a portion of the inlet and the at least one isolated flow path, and a base contacting the electrical heater conductors and the heating elements; applying a first fixed potential across the electrical heater conductors; introducing a sample to the test sensor; heating the sample at the at least two reaction zones to different temperatures in response to the potential; applying a second fixed potential across the electrical heater conductors; and analyzing the sample for the desired analyte or analytes.

Other systems, methods, features and advantages of the invention will be, or will become, apparent to one with skill in the art upon examination of the figures and detailed description. It is intended that all such additional systems, methods, features, and advantages be included within this description, be within the scope of the invention, and be protected by the claims that follow. The scope of the present invention is defined solely by the appended claims and is not affected by the statements within this summary.

DETAILED DESCRIPTION

A test sensor heating system is disclosed that provides the desired and different temperatures to at least two different reaction zones based on a fixed potential. Thus, no temperature monitoring occurs at the electrical or reaction zones, and the measurement device does not alter the potential applied to the heating system in response to temperature feedback information. Instead, the heating system provides the desired and different temperatures to the different reaction zones of the test sensor by varying heating element spacing and/or the resistivity of an associated resistive layer of the test sensor to provide the desired temperature in response to the fixed potential. The system also may provide two or more different temperature zones to the test sensor by using different heating element spacing and/or resistive layer resistivity at different locations of the test sensor. The heater includes an electrically conductive material having a variable resistance configured to generate the desired heating during the analysis. In this way, heat may be applied to one or more chemical or electrical reaction zones before, during, or after an electrical potential is applied to one or more electrical reaction zones.

FIG. 1 represents a heating system 160 including electrical heater conductors 162 configured to provide electrical communication between heating elements 164 and the measurement device (not shown). The measurement device is configured to provide at least one fixed potential to the electrical heater conductors 162. The substrate 16 of the test sensor resides on a resistive layer 168, which resides on the heating elements 164. The substrate 16 may be formed from a polymeric material having suitable flexibility for the manufacturing process. The substrate 16 supports the electrodes, conductive traces, isolated flow paths, reaction zones, and the like of the test sensor. The heating system 160 resides on base 14. The base 14 provides the test sensor with a bottom and may be formed from a polymeric material having suitable flexibility for the manufacturing process. Thus, the heating system 160 resides between the substrate 16 and the base 14, which are both preferably polymeric. Preferably, the heating system 160 is laminated between the polymers forming the test sensor substrate 16 and the test sensor base 14. Thus, the substrate 16 may be directly adhered to the base 14, or the substrate 16 may be indirectly adhered to the base 14 through the resistive layer 168.

The electrical heater conductors 162 are formed from a conductive material such as silver, gold, copper, and the like. The heating elements 164 may be formed from the same material as the electrical heater conductors 162 or from a different conductive material. Preferably, the electrical heater conductors 162 and the heating elements 164 are formed from the same conductive material, with a preferable conductive material for the conductors 162 and the elements 164 being silver.

The conductive material for the heater conductors 162 may be applied to the desired portion of the base 14 through screen-printing. Other methods including lamination followed by laser ablation, laser scribing, mechanical scribing, or photolithography may be used to form the electrical heater conductors 162 and the heating elements 164.

The resistive layer 168 is formed from a mixture of conductive and non-conductive materials selected to provide the desired resistivity to the layer 168. Screen-printing may be used to deposit the resistive layer 168 on the heating elements 164. Suitable conductive materials for the resistive layer 168 are iron, copper, aluminum, and silver, with iron being preferred at present. Suitable non-conductive materials for the resistive layer 168 are carbon and carbon mixtures, with resistive carbon being preferred at present. Resistive carbon may be obtained from Conductive Technologies Ink, York, Pa. and from DuPont, M.D., for example. Another example of resistive carbon is sold as a resistive paste by DuPont as DuPont 7292. This material has a sheet resistivity of 10 to 18 KOhm/sq.

The thicker the resistive layer 168 the more resistivity provided by the layer and the higher resistivity achieved at the same potential with the same interstitial spacing of the heating elements 164. Resistive layer thicknesses from 0.013 millimeters (mm) to 0.13 mm are presently preferred, with a nominal resistive layer thickness of 0.052 mm being more preferred at present.

Applying a fixed electrical potential to electrical heater conductors 162 of the heating system 160 causes the resistive layer 168 to warm in response to the applied potential. In this way the heating system 160 may warm the desired portion or portions of the sample before or when chemical or electrochemical reaction is occurring. FIG. 1 represents the resistive layer 168 as a single, continuous layer; however, the resistive layer 168 may include two or more portions that are not continuous, as will be discussed further below.

The temperature provided to a first reaction zone of the test sensor may be significantly different than the temperature provided to a second reaction zone of the test sensor. This is possible even though the same potential is provided by the measurement device to the electrical heater conductors 162, which energizes both the first and the second reaction zone heating elements. Thus, the voltage applied by the measurement device to the electrical heater conductors 162 of the heating system 160 results in a first set temperature at a first reaction zone of the test sensor while also providing a different second set temperature at a second reaction zone of the test sensor. The temperature provided by the heating system 160 to the substrate 16 of the test sensor as measured in the sample is preferably from 30 degrees Celsius to 90 degrees Celsius, more preferably from 35 degrees Celsius to 70 degrees Celsius.

The temperature provided by the heating system 160 in response to the voltage applied across the electrical heater conductors 162 is determined by the spacing and width of the heating elements 164 and the resistivity of the resistive layer 168.

The interstitial spacing of the heating elements 164 on which the resistive layer 168 resides may provide different temperatures with substantially the same thickness and/or ratio of conductive to non-conductive materials in the resistive layer 168 in response to the same applied voltage by altering the number of the heating elements 164 underlying an area. The greater the interstitial spacing between two consecutive heating elements, the greater the resistance between the two consecutive heating elements if the resistive layer 168 is the same material and thickness. The greater the resistance, the higher the temperature produced at the same applied voltage. Thus, different temperatures may be provided to different locations on the test sensor with the same resistive layer material ratio and thickness in response to the same applied voltage by varying the interstitial spacing of the heating elements 164.

For example, referring to FIG. 1, widely spaced, wider heating elements 163 would provide a higher temperature than closely spaced heating elements 165 with the same resistive layer in response to the same applied voltage. Thus, the test sensor of FIG. 1 would provide a higher temperature at the front than the back portion of the test strip using a continuous resistive layer having substantially the same thickness and/or ratio of conductive to non-conductive materials.

Figure 2:
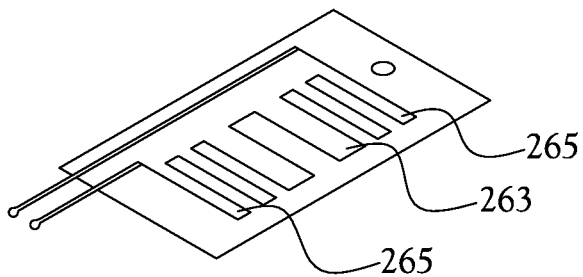
FIG. 2 represents a different heating element arrangement, where widely spaced heating elements would provide a higher temperature than closely spaced elements with the same resistive layer.

FIG. 2 represents a different heating element arrangement, where widely spaced heating elements 263 would provide a higher temperature than closely spaced elements 265 with the same resistive layer in response to the same applied voltage. Thus, the test sensor of FIG. 2 would provide a higher temperature in the middle than at the front or back.

The width of the heating elements is from 0.05 mm to 5 mm, preferably from 0.2 mm to 0.9 mm, but may be varied in accord with the applied voltage and the desired current carrying capability of the heater. Closely spaced heating elements are spaced apart from 0.05 mm to 0.56 mm, preferably from 0.2 mm to 0.56 mm, and more preferably from 0.3 mm to 0.46 mm. Wider spaced heating elements are spaced apart from 0.63 mm to 1.2 mm, preferably from 0.7 mm to 1 mm, and more preferably from 0.7 mm to 0.9 mm.

The greater the resistivity of the resistive layer 168, as represented in FIG. 1, the higher the temperature provided at the applied voltage. For example, for a given heating element spacing, a resistivity from 0.4 to 0.6 Ohm or approximately 0.5 Ohm per square millimeter may be selected for use at a selected location of the test sensor. The resistivity of the resistive layer 168 at a specific location is determined by the ratio of conductive to non-conductive materials in that location of the resistive layer 168 and/or by the thickness of the resistive layer 168 at the specific location. Other resistivities may be used by altering the material ratio and/or thickness of the resistive layer 168.

The ratio of the conductive and non-conductive materials in the resistive layer 168 can provide different temperatures with substantially the same heating element spacing in response to the same applied voltage by altering the ratio of the conductive to the non-conductive material. The ratio of the conductive to non-conductive materials in the resistive layer 168 preferably vary from 1:2 to 1:10. For example, a ratio of 1:5 for the conductive to non-conductive materials would provide more resistivity per unit area than a 1:2 mixture. The greater the resistivity per unit area, the higher the temperature at a given applied voltage.

Figure 3:
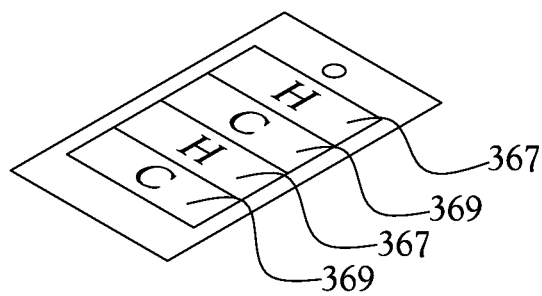
FIG. 3 represents a test sensor having cooler reaction zones provided by a greater conductive to non-conductive material ratio and hotter reaction zones provided by a lower conductive to non-conductive material ratio in response to the same potential and heating element spacing.

FIG. 3 represents a test sensor having cooler reaction zones 369 provided by a greater conductive to non-conductive material ratio (1:1 to 1:3, preferably 1:2, for example) and hotter reaction zones 367 provided by a lower conductive to non-conductive material ratio (1:4 to 1:6, preferably 1:5, for example) in response to the same applied voltage and heating element spacing. A sample entering the inlet of a test sensor in accord with FIG. 3 would first contact a higher temperature area, then a lower temperature area, then a second higher temperature area, and finally a second lower temperature area.

Figure 4:
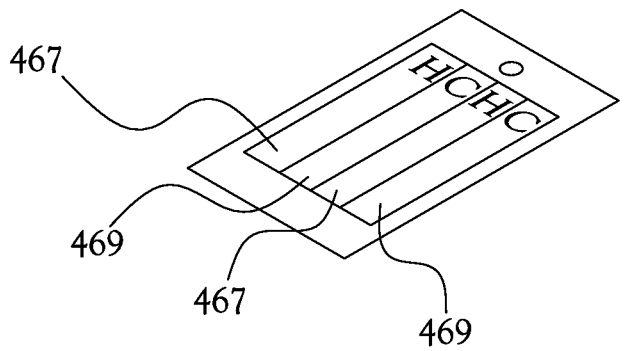
FIG. 4 represents a test sensor having cooler reaction zones provided by a greater conductive to non-conductive material ratio and hotter reaction zones provided by a lower conductive to non-conductive material ratio in response to the same potential and heating element spacing.

FIG. 4 represents a test sensor having cooler reaction zones 469 provided by a greater conductive to non-conductive material ratio (1:1 to 1:3, preferably 1:2, for example) and hotter reaction zones 467 provided by a lower conductive to non-conductive material ratio (1:4 to 1:6, preferably 1:5, for example) in response to the same applied voltage and heating element spacing. A sample entering the inlet of a test sensor in accord with FIG. 4 would enter the inlet and be divided into four isolated flow paths running parallel with the four different temperature zones, thus providing two portions of the sample with a higher temperature than the other two portions of the sample in response to the same applied voltage.

The thickness of the resistive layer 168 also may be varied to change the resistance across the layer when the same material ratio is used, or if different material ratios are used to provide additional temperature variability at the same applied voltage. The greater the thickness of the resistive layer 168, the greater the resistivity per unit area and the higher the temperature. The thickness of the resistive layer 168 may be from 0.01 mm to 0.2 mm, preferably from 0.013 mm to 0.15 mm. Other thicknesses may be used based on the desired resistivity and ratio of the conductive and non-conductive materials in the resistive layer 168.

Figure 5:
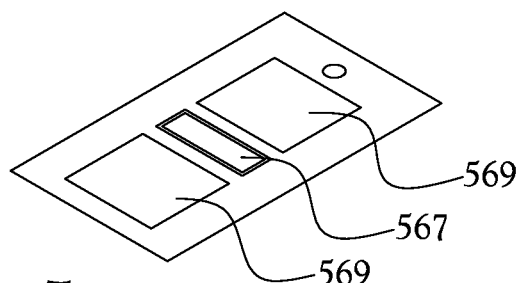
FIG. 5 represents a test sensor having two thinner resistive layers operating at lower temperature than a thicker resistive layer operating at a higher temperature in response to the same potential and heating element spacing.

FIG. 5 represents a test sensor having two thinner resistive layers 569 operating at lower temperature than a thicker resistive layer 567 operating at a higher temperature in response to the same potential and heating element spacing. A sample entering the inlet of a test sensor in accord with FIG. 5 would first contact a lower temperature area, then contact a higher temperature area, and then finally contact a second lower temperature area.

The resistive layer 168 may be formed by ink jetting or other methods. If more than one temperature is desired for different areas of the test sensor in response to a fixed potential, a less resistive material providing 50 degrees Celsius may be deposited on a first area of the test sensor while a more resistive material providing 60 degrees Celsius may be deposited on a second area of the test sensor.

The fixed potential applied across the electrical heater conductors 162 by the measurement device may be from 0.2 to 12 Volts, preferably from 0.3 to 8 Volts, and more preferably from 2 to 6 Volts. Other fixed potentials may be applied to provide the desired temperature at the reaction zones, depending on the construction and use of the heating system and test sensor. The term "fixed potential" means that the voltage applied across the electrical heater conductors 162 does not vary more than ±10% and preferably does not vary more than ±5% during the application of the selected fixed potential.

An analysis may use a single fixed potential or multiple fixed potentials, with the understanding that each fixed potential applied across the heater conductors 162 provides different temperatures to different reaction zones, if the test sensor is equipped with different temperature reaction zones. For example, if the heating system 160 heats a first reaction zone to 30 degrees Celsius and a second reaction zone to 40 degrees Celsius in response to a first fixed potential of 5 Volts applied across the electrical heater conductors 162, a second fixed potential of 8 Volts applied across the electrical heater conductors 162 may heat the first reaction zone to 40 degrees Celsius and the second reaction zone to 50 degrees Celsius.

The heating system 160 may have a resistivity from 4 to 90 Ohms, preferably from 4 to 80 Ohms, and more preferably from 4 to 60 Ohms as measured across the electrical heater conductors 162, depending on the desired reaction zone temperature in view of the fixed potential applied by the measurement device.

The measurement device includes electrical heater contacts that connect with the electrical heater conductors 162 of the test sensor to apply the potential to the heating elements that heat the sample during the analysis. The measurement device may apply the voltage to the electrical heater conductors 162 in response to the push of a button, by the insertion of the test sensor into the measurement device, or by the sample completing a circuit within the test sensor. Preferably, the measurement device applies the voltage to the heater conductors in response to the insertion of the test sensor.

The test sensor may be operated by applying a potential to the electrical heater conductors 162 and generating two different temperatures at two different locations on the test sensor. For example, if the test sensor has two chemical reaction zones through which the sample passes before reaching the analysis electrodes, the first chemical reaction zone may be heated to a different temperature than the second chemical reaction zone.

Figure 6:
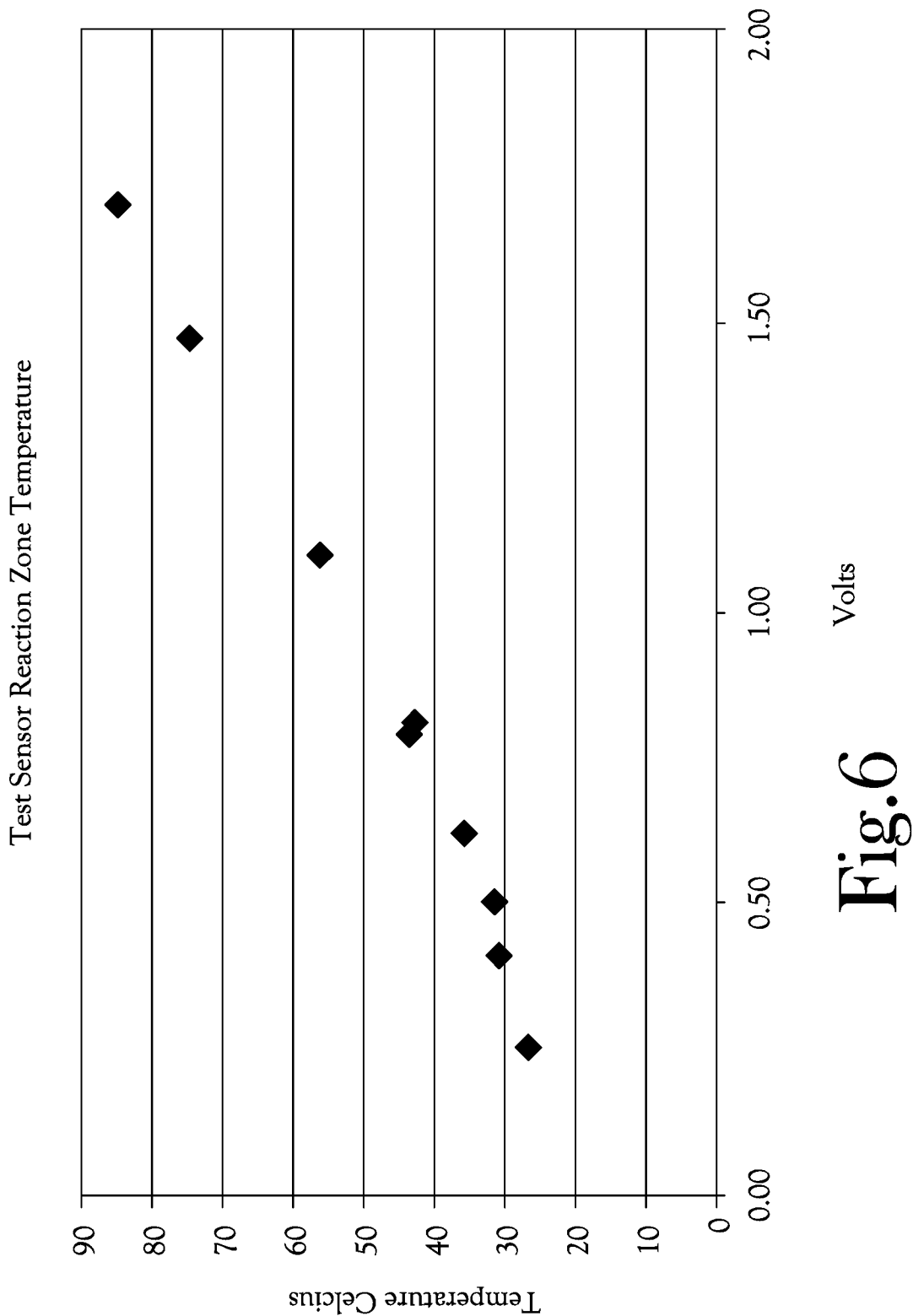
FIG. 6 is a plot relating the potential applied and the temperature generated at a reaction zone of a test sensor having heated reaction zones.

FIG. 6 is a plot relating the potential applied and the temperature generated at a reaction zone of a test sensor having heated reaction zones. The plot establishes that different applied potentials provide different reaction temps with the same interstitial spacing of heating elements, resistive layer thickness, and resistive layer ratio of conductive to non-conductive material. In this instance, the interstitial spacing of the heating elements was approximately 0.4 mm, and the resistive layer thickness was approximately 0.13 mm. As shown in the plot, reaction zone temperature increased approximately linearly in relation to the increasing applied potential with this reaction zone heater arrangement.

Figure 7:
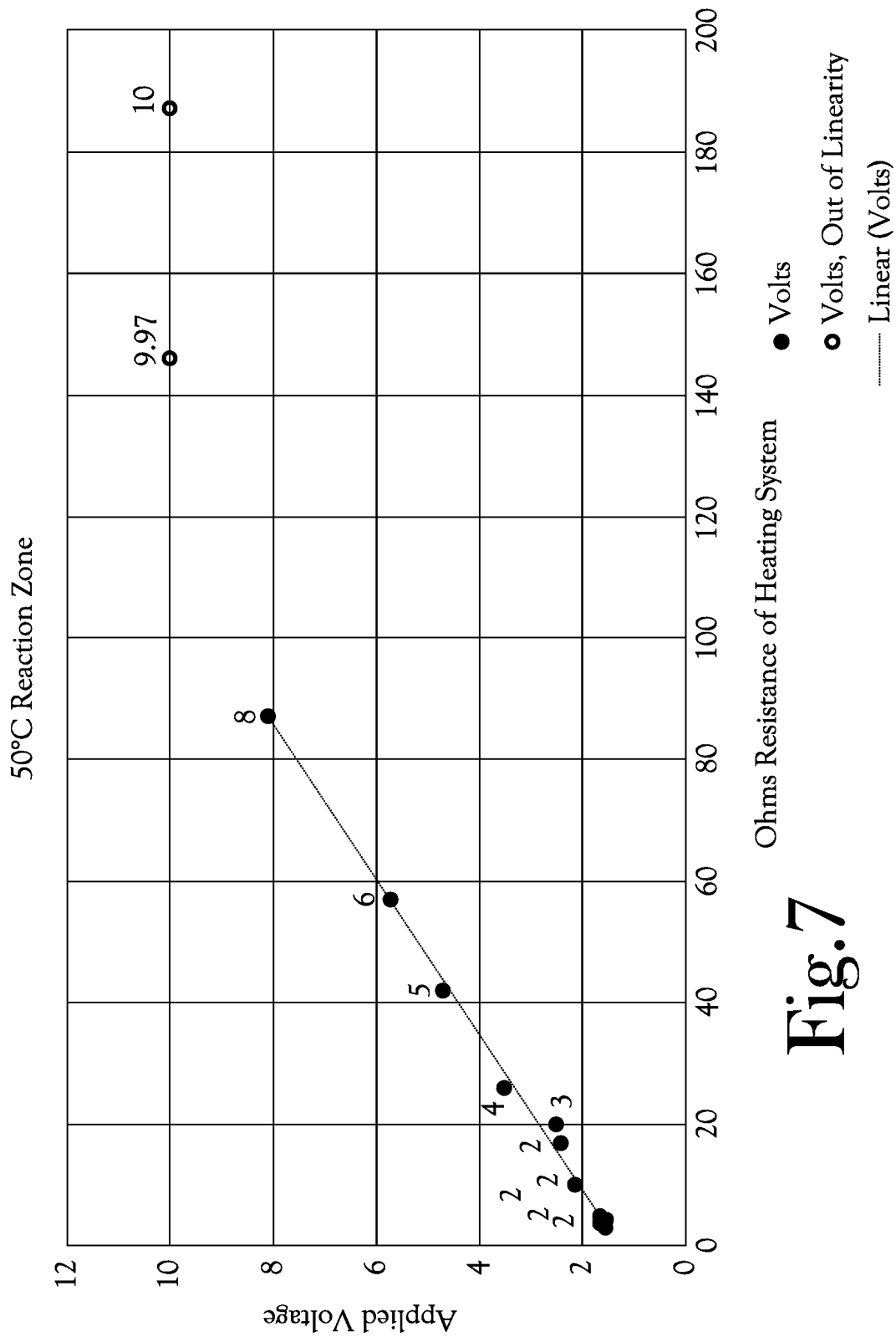
FIG. 7 is a plot relating the resistivity of the reaction zone heater in Ohms and the applied potential required to maintain an approximately 50° C. reaction zone temperature.

FIG. 7 is a plot relating the resistivity of the reaction zone heater in Ohms and the applied potential required to maintain an approximately 50° C. reaction zone temperature. As resistivity was increased in relation to FIG. 6 with a thicker resistive layer, the voltage also increased to maintain the approximately 50° C. reaction zone temperature. These reaction zone heaters lost voltage linearity above 100 Ohms. In this instance, the interstitial spacing of the heating elements was approximately 0.4 mm and the resistive layer thickness was approximately 0.13 mm. The ratio of conductive to non-conductive material in the resistive layer was approximately that of FIG. 6.

Figure 8:
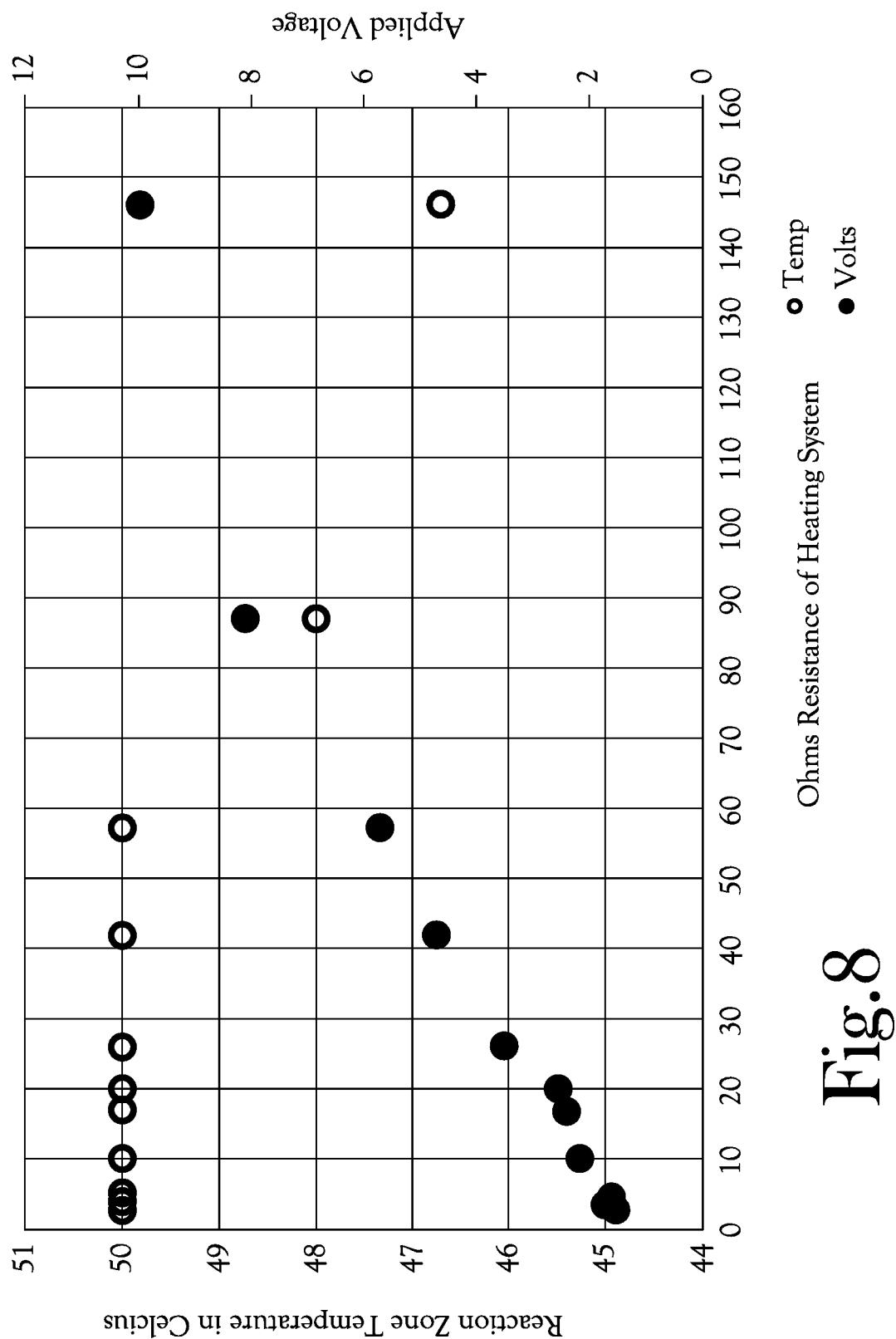
FIG. 8 is a plot relating the resistivity of the reaction zone heater in Ohms, the applied potential, and the resulting reaction zone temperature in degrees C.

FIG. 8 is a plot relating the resistivity of the reaction zone heater in Ohms, the applied potential, and the resulting reaction zone temperature in degrees C. This plot also establishes that the temperature of the reaction zone may be changed by altering the resistivity of the resistive layer.

Figure 9:
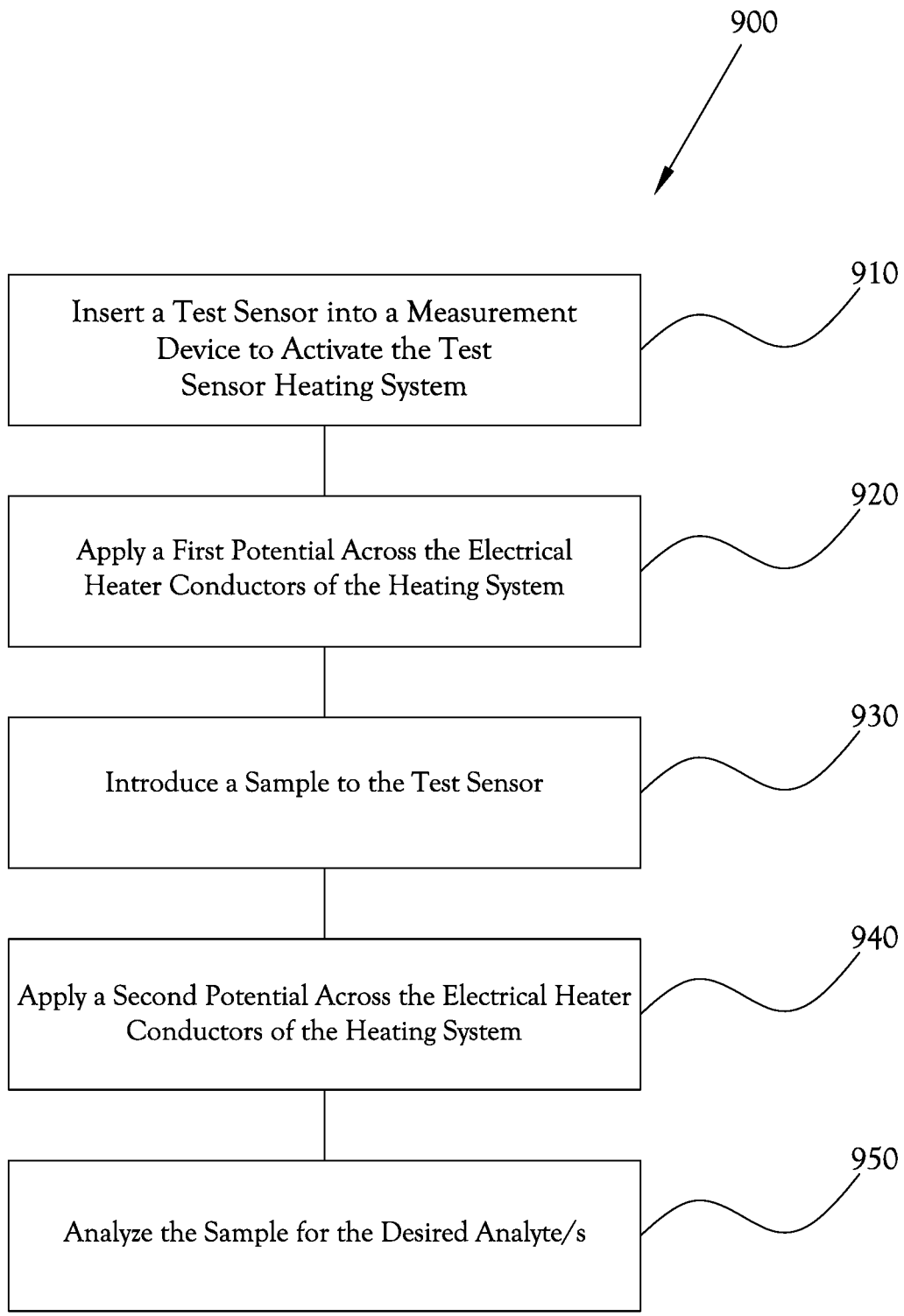
FIG. 9 represents an exemplary method of operating a heated test sensor during an analysis of a sample.

FIG. 9 represents an exemplary method 900 of operating a heated test sensor during an analysis of a sample. In 910, the test sensor is inserted into a measurement device to activate the test sensor heating system. In 920, the measurement device applies a first fixed potential across the electrical heater conductors of an approximately 40 Ohm heating system. The first fixed potential is preferably from 5.8 V to 7.2 V. In 930, a sample is introduced to the test sensor. While not represented in the figure, the heating system alternately may be activated after the sample is introduced to the test sensor. The sample preferably reaches a temperature from 30 degrees Celsius to 62 degrees Celsius within from 8 to 25 seconds of the first fixed potential being applied.

In 940, the measurement device applies a second, lower fixed potential across the electrical heater conductors of the heating system. The heating system may have a resistance of approximately 40 Ohms. The second fixed potential is preferably from 4.6 V to 5.4 V. The second fixed potential is preferably from 0.5 V to 1.5 Volts lower than the first fixed potential. The first fixed potential is switched to the second fixed potential in response to the sample contacting the contacts of a sensing electrode pair of the test sensor or in response to a fixed time after insertion of the test sensor into the measurement device or introduction of the sample to the test sensor. The fixed time is preferably from 26 to 45 seconds. Preferably, the second fixed potential maintains the temperature of the sample within ±0.5 degrees Celsius until the sample is analyzed. In 950, the measurement device analyzes the sample for the desired analyte/s.

The following examples illustrate one or more preferred embodiments of the invention. Numerous variations may be made to the following examples that lie within the scope of the invention.

EXAMPLES

Example 1: Different Temperature Zones Through Heating Element Spacing

A test sensor was formed having a heating system with one pair of heater conductors. Silver metal heating elements were screen printed onto a base. The heating element spacing underlying a first portion of the test sensor was approximately 0.38 millimeters (mm) to provide a lower temperature zone to the test sensor. The heating element interstitial spacing underlying a second portion of the test sensor was approximately 0.76 millimeters (mm) to provide a lower temperature zone to the test sensor. The width of the heating elements was approximately 0.38 mm. A single resistive layer was applied on the heating elements having a thickness of approximately 0.13 mm by screen printing. An electric potential was applied across the pair of heater conductors of approximately 4 Volts. The first portion of the test sensor heated to approximately 40 degrees Centigrade while the second portion of the test sensor heated to approximately 60 degrees Centigrade.

Prophetic Example 2: Different Temperature Zones Through Different Conductive to Non-Conductive Ratios A test sensor is formed having a heating system with one pair of heater conductors. Silver metal heating elements are screen printed onto a base. The heating element spacing underlying a first portion of the test sensor is the same as the heating element spacing underlying a second portion of the test sensor. The width of the heating elements is approximately 0.38 mm. A resistive layer is applied on the heating elements of the first portion of the test sensor having a ratio of iron to resistive carbon of 1:2 to provide a lower temperature zone to the test sensor. A resistive layer is applied on the heating elements of the second portion of the test sensor having a ratio of iron to resistive carbon of 1:10 to provide a higher temperature zone to the test sensor. The thickness of the first and the second resistive layers is about the same of approximately 0.13 mm and is applied by screen printing. An electric potential is applied across the pair of heater conductors of approximately 4 Volts. The first portion of the test sensor heats to approximately 40 degrees Centigrade while the second portion of the test sensor heats to approximately 60 degrees Centigrade.

Prophetic Example 3: Different Temperature Zones Through Different Restive Layer Thickness A test sensor is formed having a heating system with one pair of heater conductors. Silver metal heating elements are screen printed onto a base. The heating element spacing underlying a first portion of the test sensor is the same as the heating element spacing underlying a second portion of the test sensor. The width of the heating elements is approximately 0.38 mm. A resistive layer having a thickness of approximately 0.013 mm is applied on the heating elements of the first portion of the test sensor to provide a lower temperature zone to the test sensor. A resistive layer having a thickness of approximately 0.13 mm is applied on the heating elements of the first portion of the test sensor to provide a higher temperature zone to the test sensor. An electric potential is applied across the pair of heater conductors of approximately 4 Volts. The first portion of the test sensor heats to approximately 40 degrees Centigrade while the second portion of the test sensor heats to approximately 60 degrees Centigrade.

Example 4: Time, Temperature, and Voltage Correlation

Figure 10:
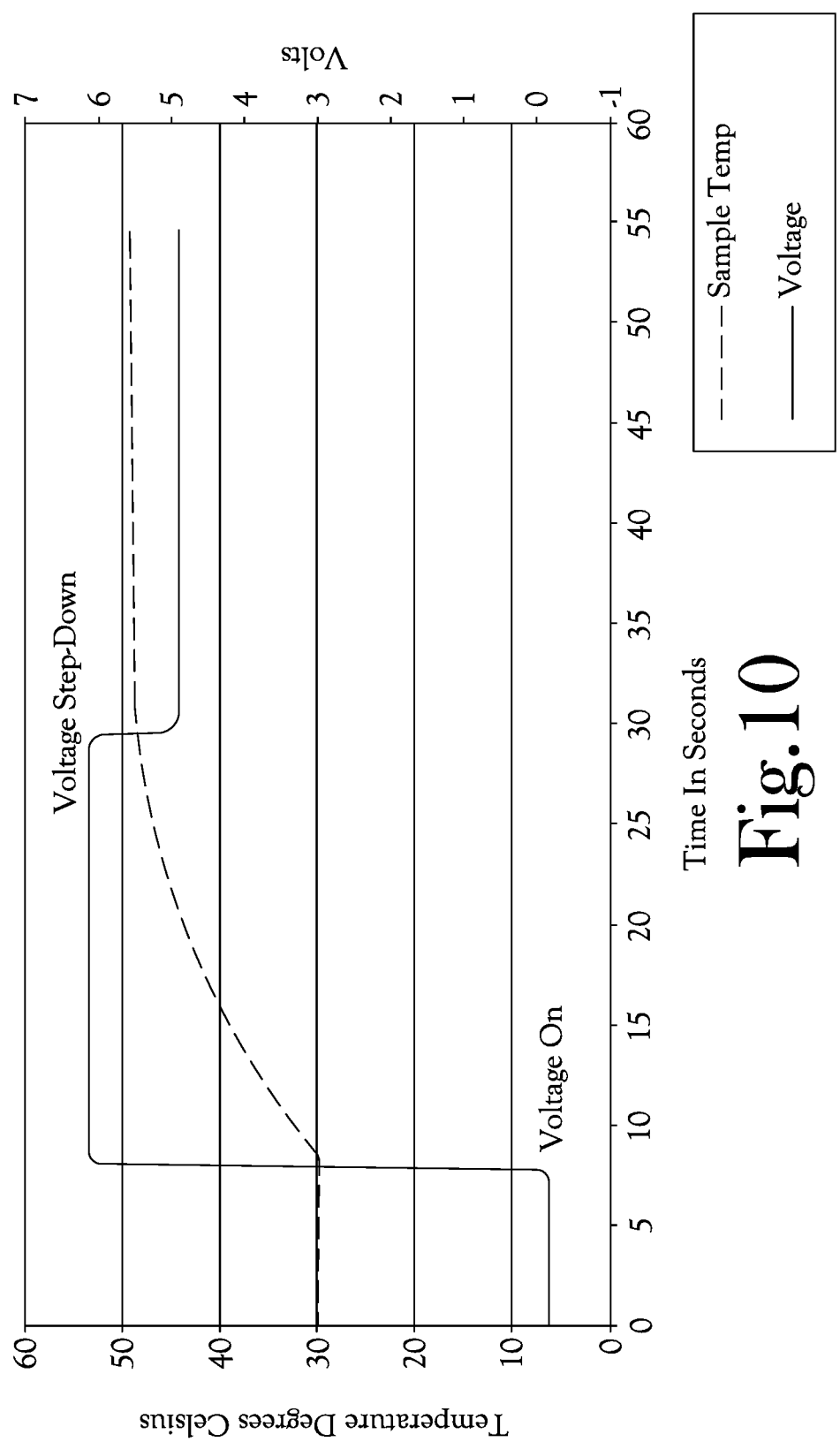
FIG. 10 is a plot relating time, sample temperature, and fixed applied voltage for a sample analysis.

A test sensor was used to determine sample heating results from the use of a first fixed applied potential and a second fixed applied potential in FIG. 10. As seen in FIG. 10, a first fixed potential of approximately 5.8 V was applied from approximately 8 to 28 seconds. Then the second, lower fixed potential was applied from approximately 28 seconds to the end of the analysis at approximately 57 seconds. The sample maintained a stable, approximately 48-49 degree Centigrade temperature after application of the second, lower fixed potential.

Unless the context clearly dictates otherwise, where a range of values is provided, each intervening value to the tenth of the unit of the lower limit between the lower limit and the upper limit of the range is included in the range of values.

While various aspects of the invention are described, it will be apparent to those of ordinary skill in the art that other embodiments and implementations are possible within the scope of the invention. Accordingly, the invention is not to be restricted except in light of the attached claims and their equivalents.

The invention claimed is:

1. A reaction zone heating system for a test sensor, the reaction zone heating system comprising:
   electrical heater conductors in electrical communication with heating elements, where the electrical heater conductors and the heating elements include a conductive material selected from the group consisting of silver, gold, copper, and combinations thereof;
   at least one resistive layer contacting the heating elements, where the resistive layer includes a mixture of conductive and non-conductive materials;
      where the mixture of conductive and non-conductive materials comprises
         a conductive material selected from the group consisting of iron, copper, aluminum, silver, and combinations thereof, and
         a non-conductive material comprising carbon;
   a substrate contacting the at least one resistive layer; and
   a base contacting the electrical heater conductors and the heating elements,
   where the reaction zone heating system is configured to heat a first reaction zone to a different temperature than a second reaction zone in response to a fixed potential applied to the same electrical heater conductors.

2. The reaction zone heating system of claim 1, where the test sensor is an electrochemical test sensor.

3. The reaction zone heating system of claim 1, where the heating elements have a width from 0.5 to 5 millimeters.

4. The reaction zone heating system of claim 1, where the heating elements have an interstitial spacing from 0.05 to 0.56 millimeters.

5. The reaction zone heating system of claim 4, further comprising heating elements having an interstitial spacing from 0.63 to 1.2 millimeters.

6. The reaction zone heating system of claim 1, where the conductive material is silver.

7. The reaction zone heating system of claim 1, where the mixture of conductive and non-conductive material has a conductive to non-conductive material ratio from 1:2 to 1:10.

8. The reaction zone heating system of claim 1, where the mixture of conductive and non-conductive materials comprises iron and resistive carbon.

9. The reaction zone heating system of claim 1, where the resistive layer has a resistivity of 0.4 to 0.6 Ohm per square millimeter.

10. The reaction zone heating system of claim 1, where the resistive layer comprises a thickness from 0.01 mm to 0.2 mm.

11. The reaction zone heating system of claim 1, where the reaction zone heating system has a resistivity from 4 Ohms to 90 Ohms as measured across the electrical heater conductors.

12. The reaction zone heating system of claim 1, where the substrate is adhered to the base directly or indirectly through the at least one resistive layer.

13. An electrochemical test sensor for analyzing a sample, the test sensor comprising:
   an inlet in fluid communication with at least one isolated flow path;
   a first reaction zone in fluid communication with the inlet;
   a second reaction zone in fluid communication with the inlet;
   a reaction zone heating system configured to transmit heat to the first reaction zone and to the second reaction zone, the reaction zone heating system comprising:
      electrical heater conductors in electrical communication with heating elements, where the electrical heater conductors and the heating elements include a conductive material selected from the group consisting of silver, gold, copper, and combinations thereof;
      at least one resistive layer contacting the heating elements, where the resistive layer includes a mixture of conductive and non-conductive materials;
         where the mixture of conductive and non-conductive materials comprises
            a conductive material selected from the group consisting of iron, copper, aluminum, silver, and combinations thereof, and
            a non-conductive material comprising carbon;
         a substrate contacting the at least one resistive layer and forming at least a portion of the inlet and the at least one isolated flow path; and
         a base contacting the electrical heater conductors and the heating elements;
   where the test sensor is configured to heat a first reaction zone to a different temperature than a second reaction zone in response to a fixed potential applied to the same electrical heater conductors.

14. The test sensor of claim 13, where the first reaction zone and the second reaction zone are in the at least one isolated flow path.

15. The test sensor of claim 13, where the at least one isolated flow path includes an electrode pair.

16. The test sensor of claim 13, further comprising a second isolated flow path where the first reaction zone is in the at least one isolated flow path and the second reaction zone is in the second isolated flow path.

17. The test sensor of claim 13, where the heating elements have a width from 0.5 to 5 millimeters.

18. The test sensor of claim 13, where the heating elements have an interstitial spacing from 0.05 to 0.56 millimeters.

19. The test sensor of claim 13, where the conductive material is silver.

20. The test sensor of claim 13, where the mixture of conductive and non-conductive material has a conductive to non-conductive material ratio from 1:2 to 1:10.

21. The test sensor of claim 13, where the mixture of conductive and non-conductive materials comprises iron and resistive carbon.

22. The test sensor of claim 13, where the resistive layer has a resistivity of 0.4 to 0.6 Ohm per square millimeter.

23. The test sensor of claim 13, where the resistive layer comprises a thickness from 0.01 mm to 0.2 mm.

24. The test sensor of claim 13, where the reaction zone heating system has a resistivity from 4 Ohms to 90 Ohms as measured across the electrical heater conductors.

25. The test sensor of claim 13, where the substrate is adhered to the base directly or indirectly through the at least one resistive layer.

26. The test sensor of claim 18, further comprising heating elements having an interstitial spacing from 0.63 to 1.2 millimeters.

\* \* \* \* \*